United States Patent [19]

Payne et al.

[11] Patent Number: 5,045,469

[45] Date of Patent: Sep. 3, 1991

[54] NOVEL BACILLUS THURINGIENSIS ISOLATE DENOTED B. T. PS81F, ACTIVE AGAINST LEPIDOPTERAN PESTS, AND A GENE ENCODING A LEPIDOPTERAN-ACTIVE TOXIN

[75] Inventors: Jewel Payne; August J. Sick, both of San Diego, Calif.

[73] Assignee: Mycogen Corporation, San Diego, Calif.

[21] Appl. No.: 263,567

[22] Filed: Oct. 27, 1988

[51] Int. Cl.[5] ........................ C12N 1/21; C12N 15/32; C12N 15/70; C12N 15/74

[52] U.S. Cl. ................................ 435/252.3; 435/69.1; 435/71.1; 435/71.3; 435/91; 435/170; 435/172.1; 435/172.3; 435/240.1; 435/320; 435/832; 435/845; 435/874; 536/27; 935/6; 935/9; 935/22; 935/59; 935/66; 935/72; 935/73

[58] Field of Search .................... 435/69.1, 71.1, 71.3, 435/91, 170, 172.1, 172.3, 240.1, 252.3, 320, 848, 874, 832; 536/27; 935/6, 9, 22, 59, 60, 61, 66, 72, 73

[56] References Cited

U.S. PATENT DOCUMENTS 4,448,885 5/1984 Schnepf et al. .
4,467,036 8/1984 Schnepf et al. .

OTHER PUBLICATIONS

H. Ernest Schnepf and H. R. Whiteley (1981), "Cloning and Expression of the Bacillus thuringiensis Crystal Protein Gene in *Escherichia coli*", Proc. Natl. Acad. Sci, USA 78(5): 2893-2897.

*Primary Examiner*—Robin L. Teskin
*Assistant Examiner*—Richard C. Peet
*Attorney, Agent, or Firm*—Saliwanchik & Saliwanchik

[57] ABSTRACT

A novel *B.t.* toxin gene toxic to lepidopteran insects has been cloned from a novel lepidopteran-active *B. thuringiensis* microbe. The DNA encoding the *B.t.* toxin can be used to transform various prokaryotic and eukaryotic microbes to express the *B.t.* toxin. These recombinant microbes can be used to control lepidopteran insects in various environments.

10 Claims, 16 Drawing Sheets a b c d a. B.t. PS81F uncut
b. B.t. PS81F cut with HindII
c. B.t. HD-1 uncut
d. B.t. HD-1 cut with HindIII

```
              10          20          30          40          50          60
   1 ATGGAGATAG TGAATAATCA GAATCAATGC GTGCCTTATA ATTGTTTAAA TAATCCTGAA
  61 AATGAGATAT TAGATATTGA AAGGTCAAAT AGTACTGTAG CAACAAACAT CGCCTTGGAG
 121 ATTAGTCGTC TGCTCGCTTC CGCAACTCCA ATAGGGGGGA TTTTATTAGG ATTGTTTGAT
 181 GCAATATGGG GGTCTATAGG CCCTTCACAA TGGGATTTAT TTTTAGAGCA AATTGAGCTA
 241 TTGATTGACC AAAAAATAGA GGAATTCGCT AGAAACCAGG CAATTTCTAG ATTAGAAGGG

             310         320         330         340         350         360
 301 ATAAGCAGTC TGTACGGAAT TTATACAGAA GCTTTTAGAG AGTGGGAAGC AGATCCTACT
 361 AATCCAGCAT TAAAAGAAGA GATGCGTACT CAATTTAATG ACATGAACAG TATTCTTGTA
 421 ACAGCTATTC CTCTTTTTTC AGTTCAAAAT TATCAAGTCC CATTTTTATC AGTATATGTT
 481 CAAGCTGCAA ATTTACATTT ATCGGTTTTG AGAGATGTTT CAGTGTTTGG GCAGGCTTGG
 541 GGATTTGATA TAGCAACAAT AAATAGTCGT TATAATGATC TGACTAGACT TATTCCTATA

             610         620         630         640         650         660
 601 TATACAGATT ATGCTGTACG CTGGTACAAT ACGGGATTAG ATCGCTTACC ACGAACTGGT
 661 GGGCTGCGAA ACTGGGCAAG ATTTAATCAG TTTAGAAGAG AGTTAACAAT ATCAGTATTA
 721 GATATTATTT CTTTTTTCAG AAATTACGAT TCTAGATTAT ATCCAATTCC AACAAGCTCC
 781 CAATTAACGC GGGAAGTATA TACAGATCCG GTAATTAATA TAACTGACTA TAGAGTTGGC
 841 CCCAGCTTCG AGAATATTGA GAACTCAGCC ATTAGAAGCC CCCACCTTAT GGACTTCTTA

             910         920         930         940         950         960
 901 AATAATTTGA CCATTGATAC GGATTTGATT AGAGGTGTTC ACTATTGGGC AGGGCATCGT
 961 GTAACTTCTC ATTTTACAGG TAGTTCTCAA GTGATAACAA CCCCTCAATA TGGGATAACC
1021 GCAAATGCGG AACCAAGACG AACTATTGCT CCTAGTACTT TTCCAGGTCT TAACCTATTT
1081 TATAGAACAT TATCAAATCC TTTCTTCCGA AGATCAGAAA ATATTACTCC TACCTTAGGG
1141 ATAAATGTAG TACAGGGAGT AGGGTTCATT CAACCAAATA ATGCTGAAGT TCTATATAGA

            1210        1220        1230        1240        1250        1260
1201 AGTAGGGGGA CAGTAGATTC TCTTAATGAG TTACCAATTG ATGGTGAGAA TTCATTAGTT
1261 GGATATAGTC ATCGATTAAG TCATGTTACA CTAACCAGGT CGTTATATAA TACTAATATA
1321 ACTAGCCTGC CAACATTTGT TTGGACACAT CACAGTGCTA CTAATACAAA TACAATTAAT
1381 CCAGATATTA TTACACAAAT ACCTTTAGTG AAAGGATTTA GACTTGGTGG TGGCACCTCT
1441 GTCATTAAAG GACCAGGATT TACAGGAGGG GATATCCTTC GAAGAAATAC CATTGGTGAG

            1510        1520        1530        1540        1550        1560
1501 TTTGTGTCTT TACAAGTCAA TATTAACTCA CCAATTACCC AAAGATACCG TTTAAGATTT
1561 CGTTATGCTT CCAGTAGGGA TGCACGAATT ACTGTAGCGA TAGGAGGACA AATTAGAGTA
1621 GATATGACCC TTGAAAAAAC CATGGAAATT GGGGAGAGCT TAACATCTAG AACATTTAGC
1681 TATACCAATT TTAGTAATCC TTTTTCATTT AGGGCTAATC CAGATATAAT TAGAATAGCT
1741 GAAGAACTTC CTATTCGTGG TGGTGAGCTT TATATAGATA AAATTGAACT TATTCTAGCA
```

FIG.2-1

```
           1810       1820       1830       1840       1850       1860
1801 GATGCAACAT TTGAAGAAGA ATATGATTTG GAAAGAGCAC AGAAGGCGGT GAATGCCCTG
1861 TTTACTTCTA CAAATCAACT AGGGCTAAAA ACAGATGTGA CGGATTATCA TATTGATCAA
1921 GTTTCCAATT TAGTTGAGTG TTTATCGGAT GAATTTTGTC TGGATGAAAA GAGAGAATTA
1981 TCCGAGAAAG TCAAACATGC GAAGCGACTC AGTGATGAAC GGAATTTACT TCAAGATCCA
2041 AACTTCAGAG GGATCAATAG GCAACCAGAC CGTGGCTGGA GAGGAAGCAC GGATATTACT

           2110       2120       2130       2140       2150       2160
2101 ATCCAAGGTG GAGATGACGT ATTCAAAGAG AATTACGTCA CATTACCGGG TACCTTTGAT
2161 GAGTGCTATC CAACGTATTT ATATCAAAAA ATAGATGAGT CGAAGTTAAA AGCTTATACC
2221 CGCTATGAAT TAAGAGGGTA TATCGAGGAT AGTCAAGACT TAGAAATCTA TTTAATTCGC
2281 TACAATGCAA AACACGAGAC AGTAAACGTG CCAGGTACGG GTTCCTTATG GCCGCTTTCA
2341 GCCCAAAGTC CAATCGGAAA GTGTGGAGAA CCGAATCGAT GCGCGCCACA CCTTGAATGG

           2410       2420       2430       2440       2450       2460
2401 AATCCTAATC TAGATTGCTC CTGCAGAGAC GGGGAAAAAT GTGCCCATCA TTCCCATCAT
2461 TTCTCCTTGG ACATTGATGT TGGATGTACA GACTTAAATG AGGACTTAGG TGTATGGGTG
2521 ATATTCAAGA TTAAGACACA AGATGGCTAT GCAAGACTAG GAAATCTAGA GTTTCTCGAA
2581 GAGAAACCAC TATTAGGGGA AGCACTAGCT CGTGTGAAAA GAGCGGAGAA AAAATGGAGA
2641 GACAAATGCG AAAAATTGGA ATGGGAAACA AATATTGTTT ATAAAGAGGC AAAAGAATCT

           2710       2720       2730       2740       2750       2760
2701 GTAGATGCTT TATTTGTAAA CTCTCAATAT GATAGATTAC AAGCGGATAC GAATATCGCG
2761 ATGATTCATG CGGCAGATAA ACGCGTTCAT AGCATTCGAG AAGCGTATCT GCCAGAGCTG
2821 TCTGTGATTC CGGGTGTCAA TGCGGCTATT TTTGAAGAAT TAGAAGGGCG TATTTTCACT
2881 GCATTCTCCC TATATGATGC GAGAAATGTC ATTAAAAATG GCGATTTCAA TAATGGCTTA
2941 TCATGCTGGA ACGTGAAAGG GCATGTAGAT GTAGAAGAAC AGAACAACCA TCGTTCGGTC

           3010       3020       3030       3040       3050       3060
3001 CTTGTTGTTC CAGAATGGGA AGCAGAAGTG TCACAAGAAG TTCGTGTTTG TCCGGGTCGT
3061 GGCTATATCC TTCGTGTTAC AGCGTACAAA GAGGGATATG GAGAGGGCTG TGTAACGATT
3121 CATGAGATCG AAGACAATAC AGACGAACTG AAATTCAGCA ACTGTGTAGA AGAGGAAGTA
3181 TATCCAAACA ACACGGTAAC GTGTAATAAT TATACTGCGA CTCAAGAAGA ACATGAGGGT
3241 ACGTACACTT CCCGTAATCG AGGATATGAC GAAGCCTATG AAAGCAATTC TTCTGTACAT

           3310       3320       3330       3340       3350       3360
3301 GCGTCAGTCT ATGAAGAAAA ATCGTATACA GATAGACGAA GAGAGAATCC TTGTGAATCT
3361 AACAGAGGAT ATGGGGATTA CACACCACTA CCAGCTGGCT ATGTGACAAA AGAATTAGAG
3421 TACTTCCCAG AAACCGATAA GGTATGGATT GAGATCGGAG AAACGGAAGG AACATTCATC
3481 GTGGACAGCG TGGAATTACT TCTTATGGAG GAATAATA
```

FIG. 2-2

| | | | | | 5 | | | | | 10 | | | | | 15 |
|---|---|---|---|---|---|---|---|---|---|---|---|---|---|---|---|
| 1 | Met | Glu | Ile | Val | Asn | Asn | Gln | Asn | Gln | Cys | Val | Pro | Tyr | Asn | Cys |
| 16 | Leu | Asn | Asn | Pro | Glu | Asn | Glu | Ile | Leu | Asp | Ile | Glu | Arg | Ser | Asn |
| 31 | Ser | Thr | Val | Ala | Thr | Asn | Ile | Ala | Leu | Glu | Ile | Ser | Arg | Leu | Leu |
| 46 | Ala | Ser | Ala | Thr | Pro | Ile | Gly | Gly | Ile | Leu | Leu | Gly | Leu | Phe | Asp |
| 61 | Ala | Ile | Trp | Gly | Ser | Ile | Gly | Pro | Ser | Gln | Trp | Asp | Leu | Phe | Leu |
| 76 | Glu | Gln | Ile | Glu | Leu | Leu | Ile | Asp | Gln | Lys | Ile | Glu | Glu | Phe | Ala |
| 91 | Arg | Asn | Gln | Ala | Ile | Ser | Arg | Leu | Glu | Gly | Ile | Ser | Ser | Leu | Tyr |
| 106 | Gly | Ile | Tyr | Thr | Glu | Ala | Phe | Arg | Glu | Trp | Glu | Ala | Asp | Pro | Thr |
| 121 | Asn | Pro | Ala | Leu | Lys | Glu | Glu | Met | Arg | Thr | Gln | Phe | Asn | Asp | Met |
| 136 | Asn | Ser | Ile | Leu | Val | Thr | Ala | Ile | Pro | Leu | Phe | Ser | Val | Gln | Asn |
| 151 | Tyr | Gln | Val | Pro | Phe | Leu | Ser | Val | Tyr | Val | Gln | Ala | Ala | Asn | Leu |
| 166 | His | Leu | Ser | Val | Leu | Arg | Asp | Val | Ser | Val | Phe | Gly | Gln | Ala | Trp |
| 181 | Gly | Phe | Asp | Ile | Ala | Thr | Ile | Asn | Ser | Arg | Tyr | Asn | Asp | Leu | Thr |
| 196 | Arg | Leu | Ile | Pro | Ile | Tyr | Thr | Asp | Tyr | Ala | Val | Arg | Trp | Tyr | Asn |
| 211 | Thr | Gly | Leu | Asp | Arg | Leu | Pro | Arg | Thr | Gly | Gly | Leu | Arg | Asn | Trp |
| 226 | Ala | Arg | Phe | Asn | Gln | Phe | Arg | Arg | Glu | Leu | Thr | Ile | Ser | Val | Leu |
| 241 | Asp | Ile | Ile | Ser | Phe | Phe | Arg | Asn | Tyr | Asp | Ser | Arg | Leu | Tyr | Pro |
| 256 | Ile | Pro | Thr | Ser | Ser | Gln | Leu | Thr | Arg | Glu | Val | Tyr | Thr | Asp | Pro |
| 271 | Val | Ile | Asn | Ile | Thr | Asp | Tyr | Arg | Val | Gly | Pro | Ser | Phe | Glu | Asn |
| 286 | Ile | Glu | Asn | Ser | Ala | Ile | Arg | Ser | Pro | His | Leu | Met | Asp | Phe | Leu |
| 301 | Asn | Asn | Leu | Thr | Ile | Asp | Thr | Asp | Leu | Ile | Arg | Gly | Val | His | Tyr |
| 316 | Trp | Ala | Gly | His | Arg | Val | Thr | Ser | His | Phe | Thr | Gly | Ser | Ser | Gln |
| 331 | Val | Ile | Thr | Thr | Pro | Gln | Tyr | Gly | Ile | Thr | Ala | Asn | Ala | Glu | Pro |
| 346 | Arg | Arg | Thr | Ile | Ala | Pro | Ser | Thr | Phe | Pro | Gly | Leu | Asn | Leu | Phe |
| 361 | Tyr | Arg | Thr | Leu | Ser | Asn | Pro | Phe | Phe | Arg | Arg | Ser | Glu | Asn | Ile |
| 376 | Thr | Pro | Thr | Leu | Gly | Ile | Asn | Val | Val | Gln | Gly | Val | Gly | Phe | Ile |
| 391 | Gln | Pro | Asn | Asn | Ala | Glu | Val | Leu | Tyr | Arg | Ser | Arg | Gly | Thr | Val |
| 406 | Asp | Ser | Leu | Asn | Glu | Leu | Pro | Ile | Asp | Gly | Glu | Asn | Ser | Leu | Val |
| 421 | Gly | Tyr | Ser | His | Arg | Leu | Ser | His | Val | Thr | Leu | Thr | Arg | Ser | Leu |
| 436 | Tyr | Asn | Thr | Asn | Ile | Thr | Ser | Leu | Pro | Thr | Phe | Val | Trp | Thr | His |
| 451 | His | Ser | Ala | Thr | Asn | Thr | Asn | Thr | Ile | Asn | Pro | Asp | Ile | Ile | Thr |
| 466 | Gln | Ile | Pro | Leu | Val | Lys | Gly | Phe | Arg | Leu | Gly | Gly | Gly | Thr | Ser |
| 481 | Val | Ile | Lys | Gly | Pro | Gly | Phe | Thr | Gly | Gly | Asp | Ile | Leu | Arg | Arg |
| 496 | Asn | Thr | Ile | Gly | Glu | Phe | Val | Ser | Leu | Gln | Val | Asn | Ile | Asn | Ser |
| 511 | Pro | Ile | Thr | Gln | Arg | Tyr | Arg | Leu | Arg | Phe | Arg | Tyr | Ala | Ser | Ser |
| 526 | Arg | Asp | Ala | Arg | Ile | Thr | Val | Ala | Ile | Gly | Gly | Gln | Ile | Arg | Val |
| 541 | Asp | Met | Thr | Leu | Glu | Lys | Thr | Met | Glu | Ile | Gly | Glu | Ser | Leu | Thr |
| 556 | Ser | Arg | Thr | Phe | Ser | Tyr | Thr | Asn | Phe | Ser | Asn | Pro | Phe | Ser | Phe |
| 571 | Arg | Ala | Asn | Pro | Asp | Ile | Ile | Arg | Ile | Ala | Glu | Glu | Leu | Pro | Ile |
| 586 | Arg | Gly | Gly | Glu | Leu | Tyr | Ile | Asp | Lys | Ile | Glu | Leu | Ile | Leu | Ala |

FIG.3-1

601 Asp Ala Thr Phe Glu Glu Glu Tyr Asp Leu Glu Arg Ala Gln Lys
616 Ala Val Asn Ala Leu Phe Thr Ser Thr Asn Gln Leu Gly Leu Lys
631 Thr Asp Val Thr Asp Tyr His Ile Asp Gln Val Ser Asn Leu Val
646 Glu Cys Leu Ser Asp Glu Phe Cys Leu Asp Glu Lys Arg Glu Leu
661 Ser Glu Lys Val Lys His Ala Lys Arg Leu Ser Asp Glu Arg Asn
676 Leu Leu Gln Asp Pro Asn Phe Arg Gly Ile Asn Arg Gln Pro Asp
691 Arg Gly Trp Arg Gly Ser Thr Asp Ile Thr Ile Gln Gly Gly Asp
706 Asp Val Phe Lys Glu Asn Tyr Val Thr Leu Pro Gly Thr Phe Asp
721 Glu Cys Tyr Pro Thr Tyr Leu Tyr Gln Lys Ile Asp Glu Ser Lys
736 Leu Lys Ala Tyr Thr Arg Tyr Glu Leu Arg Gly Tyr Ile Glu Asp
751 Ser Gln Asp Leu Glu Ile Tyr Leu Ile Arg Tyr Asn Ala Lys His
766 Glu Thr Val Asn Val Pro Gly Thr Gly Ser Leu Trp Pro Leu Ser
781 Ala Gln Ser Pro Ile Gly Lys Cys Gly Glu Pro Asn Arg Cys Ala
796 Pro His Leu Glu Trp Asn Pro Asn Leu Asp Cys Ser Cys Arg Asp
811 Gly Glu Lys Cys Ala His His Ser His His Phe Ser Leu Asp Ile
826 Asp Val Gly Cys Thr Asp Leu Asn Glu Asp Leu Gly Val Trp Val
841 Ile Phe Lys Ile Lys Thr Gln Asp Gly Tyr Ala Arg Leu Gly Asn
856 Leu Glu Phe Leu Glu Glu Lys Pro Leu Leu Gly Glu Ala Leu Ala
871 Arg Val Lys Arg Ala Glu Lys Lys Trp Arg Asp Lys Cys Glu Lys
886 Leu Glu Trp Glu Thr Asn Ile Val Tyr Lys Glu Ala Lys Glu Ser
901 Val Asp Ala Leu Phe Val Asn Ser Gln Tyr Asp Arg Leu Gln Ala
916 Asp Thr Asn Ile Ala Met Ile His Ala Ala Asp Lys Arg Val His
931 Ser Ile Arg Glu Ala Tyr Leu Pro Glu Leu Ser Val Ile Pro Gly
946 Val Asn Ala Ala Ile Phe Glu Glu Leu Glu Gly Arg Ile Phe Thr
961 Ala Phe Ser Leu Tyr Asp Ala Arg Asn Val Ile Lys Asn Gly Asp
976 Phe Asn Asn Gly Leu Ser Cys Trp Asn Val Lys Gly His Val Asp
991 Val Glu Glu Gln Asn Asn His Arg Ser Val Leu Val Val Pro Glu
1006 Trp Glu Ala Glu Val Ser Gln Glu Val Arg Val Cys Pro Gly Arg
1021 Gly Tyr Ile Leu Arg Val Thr Ala Tyr Lys Glu Gly Tyr Gly Glu
1036 Gly Cys Val Thr Ile His Glu Ile Glu Asp Asn Thr Asp Glu Leu
1051 Lys Phe Ser Asn Cys Val Glu Glu Glu Val Tyr Pro Asn Asn Thr
1066 Val Thr Cys Asn Asn Tyr Thr Ala Thr Gln Glu Glu His Glu Gly
1081 Thr Tyr Thr Ser Arg Asn Arg Gly Tyr Asp Glu Ala Tyr Glu Ser
1096 Asn Ser Ser Val His Ala Ser Val Tyr Glu Glu Lys Ser Tyr Thr
1111 Asp Arg Arg Arg Glu Asn Pro Cys Glu Ser Asn Arg Gly Tyr Gly
1126 Asp Tyr Thr Pro Leu Pro Ala Gly Tyr Val Thr Lys Glu Leu Glu
1141 Tyr Phe Pro Glu Thr Asp Lys Val Trp Ile Glu Ile Gly Glu Thr
1156 Glu Gly Thr Phe Ile Val Asp Ser Val Glu Leu Leu Leu Met Glu
1171 Glu

FIG.3-2

| | | | | | | | | | | | | | | | | | | | |
|---|---|---|---|---|---|---|---|---|---|---|---|---|---|---|---|---|---|---|---|
| | | | | 5 | | | | | 10 | | | | | 15 | | | | | 20 |
| Met | Glu | Ile | Val | Asn | Asn | Gln | Asn | Gln | Cys | Val | Pro | Tyr | Asn | Cys | Leu | Asn | Asn | Pro | Glu |
| ATG | GAG | ATA | GTG | AAT | AAT | CAG | AAT | CAA | TGC | GTG | CCT | TAT | AAT | TGT | TTA | AAT | AAT | CCT | GAA |
| | | | | 25 | | | | | 30 | | | | | 35 | | | | | 40 |
| Asn | Glu | Ile | Leu | Asp | Ile | Glu | Arg | Ser | Asn | Ser | Thr | Val | Ala | Thr | Asn | Ile | Ala | Leu | Glu |
| AAT | GAG | ATA | TTA | GAT | ATT | GAA | AGG | TCA | AAT | AGT | ACT | GTA | GCA | ACA | AAC | ATC | GCC | TTG | GAG |
| | | | | 45 | | | | | 50 | | | | | 55 | | | | | 60 |
| Ile | Ser | Arg | Leu | Leu | Ala | Ser | Ala | Thr | Pro | Ile | Gly | Gly | Ile | Leu | Leu | Gly | Leu | Phe | Asp |
| ATT | AGT | CGT | CTG | CTC | GCT | TCC | GCA | ACT | CCA | ATA | GGG | GGG | ATT | TTA | TTA | GGA | TTG | TTT | GAT |
| | | | | 65 | | | | | 70 | | | | | 75 | | | | | 80 |
| Ala | Ile | Trp | Gly | Ser | Ile | Gly | Pro | Ser | Gln | Trp | Asp | Leu | Phe | Leu | Glu | Gln | Ile | Glu | Leu |
| GCA | ATA | TGG | GGG | TCT | ATA | GGC | CCT | TCA | CAA | TGG | GAT | TTA | TTT | TTA | GAG | CAA | ATT | GAG | CTA |
| | | | | 85 | | | | | 90 | | | | | 95 | | | | | 100 |
| Leu | Ile | Asp | Gln | Lys | Ile | Glu | Glu | Phe | Ala | Arg | Asn | Gln | Ala | Ile | Ser | Arg | Leu | Glu | Gly |
| TTG | ATT | GAC | CAA | AAA | ATA | GAG | GAA | TTC | GCT | AGA | AAC | CAG | GCA | ATT | TCT | AGA | TTA | GAA | GGG |
| | | | | 105 | | | | | 110 | | | | | 115 | | | | | 120 |
| Ile | Ser | Ser | Leu | Tyr | Gly | Ile | Tyr | Thr | Glu | Ala | Phe | Arg | Glu | Trp | Glu | Ala | Asp | Pro | Thr |
| ATA | AGC | AGT | CTG | TAC | GGA | ATT | TAT | ACA | GAA | GCT | TTT | AGA | GAG | TGG | GAA | GCA | GAT | CCT | ACT |
| | | | | 125 | | | | | 130 | | | | | 135 | | | | | 140 |
| Asn | Pro | Ala | Leu | Lys | Glu | Glu | Met | Arg | Thr | Gln | Phe | Asn | Asp | Met | Asn | Ser | Ile | Leu | Val |
| AAT | CCA | GCA | TTA | AAA | GAA | GAG | ATG | CGT | ACT | CAA | TTT | AAT | GAC | ATG | AAC | AGT | ATT | CTT | GTA |
| | | | | 145 | | | | | 150 | | | | | 155 | | | | | 160 |
| Thr | Ala | Ile | Pro | Leu | Phe | Ser | Val | Gln | Asn | Tyr | Gln | Val | Pro | Phe | Leu | Ser | Val | Tyr | Val |
| ACA | GCT | ATT | CCT | CTT | TTT | TCA | GTT | CAA | AAT | TAT | CAA | GTC | CCA | TTT | TTA | TCA | GTA | TAT | GTT |
| | | | | 165 | | | | | 170 | | | | | 175 | | | | | 180 |
| Gln | Ala | Ala | Asn | Leu | His | Leu | Ser | Val | Leu | Arg | Asp | Val | Ser | Val | Phe | Gly | Gln | Ala | Trp |
| CAA | GCT | GCA | AAT | TTA | CAT | TTA | TCG | GTT | TTG | AGA | GAT | GTT | TCA | GTG | TTT | GGG | CAG | GCT | TGG |
| | | | | 185 | | | | | 190 | | | | | 195 | | | | | 200 |
| Gly | Phe | Asp | Ile | Ala | Thr | Ile | Asn | Ser | Arg | Tyr | Asn | Asp | Leu | Thr | Arg | Leu | Ile | Pro | Ile |
| GGA | TTT | GAT | ATA | GCA | ACA | ATA | AAT | AGT | CGT | TAT | AAT | GAT | CTG | ACT | AGA | CTT | ATT | CCT | ATA |
| | | | | 205 | | | | | 210 | | | | | 215 | | | | | 220 |
| Tyr | Thr | Asp | Tyr | Ala | Val | Arg | Trp | Tyr | Asn | Thr | Gly | Leu | Asp | Arg | Leu | Pro | Arg | Thr | Gly |
| TAT | ACA | GAT | TAT | GCT | GTA | CGC | TGG | TAC | AAT | ACG | GGA | TTA | GAT | CGC | TTA | CCA | CGA | ACT | GGT |
| | | | | 225 | | | | | 230 | | | | | 235 | | | | | 240 |
| Gly | Leu | Arg | Asn | Trp | Ala | Arg | Phe | Asn | Gln | Phe | Arg | Arg | Glu | Leu | Thr | Ile | Ser | Val | Leu |
| GGG | CTG | CGA | AAC | TGG | GCA | AGA | TTT | AAT | CAG | TTT | AGA | AGA | GAG | TTA | ACA | ATA | TCA | GTA | TTA |
| | | | | 245 | | | | | 250 | | | | | 255 | | | | | 260 |
| Asp | Ile | Ile | Ser | Phe | Phe | Arg | Asn | Tyr | Asp | Ser | Arg | Leu | Tyr | Pro | Ile | Pro | Thr | Ser | Ser |
| GAT | ATT | ATT | TCT | TTT | TTC | AGA | AAT | TAC | GAT | TCT | AGA | TTA | TAT | CCA | ATT | CCA | ACA | AGC | TCC |
| | | | | 265 | | | | | 270 | | | | | 275 | | | | | 280 |
| Gln | Leu | Thr | Arg | Glu | Val | Tyr | Thr | Asp | Pro | Val | Ile | Asn | Ile | Thr | Asp | Tyr | Arg | Val | Gly |
| CAA | TTA | ACG | CGG | GAA | GTA | TAT | ACA | GAT | CCG | GTA | ATT | AAT | ATA | ACT | GAC | TAT | AGA | GTT | GGC |
| | | | | 285 | | | | | 290 | | | | | 295 | | | | | 300 |
| Pro | Ser | Phe | Glu | Asn | Ile | Glu | Asn | Ser | Ala | Ile | Arg | Ser | Pro | His | Leu | Met | Asp | Phe | Leu |
| CCC | AGC | TTC | GAG | AAT | ATT | GAG | AAC | TCA | GCC | ATT | AGA | AGC | CCC | CAC | CTT | ATG | GAC | TTC | TTA |

FIG.4-1

```
                305                 310                 315                 320
Asn Asn Leu Thr Ile Asp Thr Asp Leu Ile Arg Gly Val His Tyr Trp Ala Gly His Arg
AAT AAT TTG ACC ATT GAT ACG GAT TTG ATT AGA GGT GTT CAC TAT TGG GCA GGG CAT CGT

                325                 330                 335                 340
Val Thr Ser His Phe Thr Gly Ser Ser Gln Val Ile Thr Thr Pro Gln Tyr Gly Ile Thr
GTA ACT TCT CAT TTT ACA GGT AGT TCT CAA GTG ATA ACA ACC CCT CAA TAT GGG ATA ACC

                345                 350                 355                 360
Ala Asn Ala Glu Pro Arg Arg Thr Ile Ala Pro Ser Thr Phe Pro Gly Leu Asn Leu Phe
GCA AAT GCG GAA CCA AGA CGA ACT ATT GCT CCT AGT ACT TTT CCA GGT CTT AAC CTA TTT

                365                 370                 375                 380
Tyr Arg Thr Leu Ser Asn Pro Phe Phe Arg Arg Ser Glu Asn Ile Thr Pro Thr Leu Gly
TAT AGA ACA TTA TCA AAT CCT TTC TTC CGA AGA TCA GAA AAT ATT ACT CCT ACC TTA GGG

                385                 390                 395                 400
Ile Asn Val Val Gln Gly Val Gly Phe Ile Gln Pro Asn Asn Ala Glu Val Leu Tyr Arg
ATA AAT GTA GTA CAG GGA GTA GGG TTC ATT CAA CCA AAT AAT GCT GAA GTT CTA TAT AGA

                405                 410                 415                 420
Ser Arg Gly Thr Val Asp Ser Leu Asn Glu Leu Pro Ile Asp Gly Glu Asn Ser Leu Val
AGT AGG GGG ACA GTA GAT TCT CTT AAT GAG TTA CCA ATT GAT GGT GAG AAT TCA TTA GTT

                425                 430                 435                 440
Gly Tyr Ser His Arg Leu Ser His Val Thr Leu Thr Arg Ser Leu Tyr Asn Thr Asn Ile
GGA TAT AGT CAT CGA TTA AGT CAT GTT ACA CTA ACC AGG TCG TTA TAT AAT ACT AAT ATA

                445                 450                 455                 460
Thr Ser Leu Pro Thr Phe Val Trp Thr His His Ser Ala Thr Asn Thr Asn Thr Ile Asn
ACT AGC CTG CCA ACA TTT GTT TGG ACA CAT CAC AGT GCT ACT AAT ACA AAT ACA ATT AAT

                465                 470                 475                 480
Pro Asp Ile Ile Thr Gln Ile Pro Leu Val Lys Gly Phe Arg Leu Gly Gly Gly Thr Ser
CCA GAT ATT ATT ACA CAA ATA CCT TTA GTG AAA GGA TTT AGA CTT GGT GGT GGC ACC TCT

                485                 490                 495                 500
Val Ile Lys Gly Pro Gly Phe Thr Gly Gly Asp Ile Leu Arg Arg Asn Thr Ile Gly Glu
GTC ATT AAA GGA CCA GGA TTT ACA GGA GGG GAT ATC CTT CGA AGA AAT ACC ATT GGT GAG

                505                 510                 515                 520
Phe Val Ser Leu Gln Val Asn Ile Asn Ser Pro Ile Thr Gln Arg Tyr Arg Leu Arg Phe
TTT GTG TCT TTA CAA GTC AAT ATT AAC TCA CCA ATT ACC CAA AGA TAC CGT TTA AGA TTT

                525                 530                 535                 540
Arg Tyr Ala Ser Ser Arg Asp Ala Arg Ile Thr Val Ala Ile Gly Gly Gln Ile Arg Val
CGT TAT GCT TCC AGT AGG GAT GCA CGA ATT ACT GTA GCG ATA GGA GGA CAA ATT AGA GTA

                545                 550                 555                 560
Asp Met Thr Leu Glu Lys Thr Met Glu Ile Gly Glu Ser Leu Thr Ser Arg Thr Phe Ser
GAT ATG ACC CTT GAA AAA ACC ATG GAA ATT GGG GAG AGC TTA ACA TCT AGA ACA TTT AGC

                565                 570                 575                 580
Tyr Thr Asn Phe Ser Asn Pro Phe Ser Phe Arg Ala Asn Pro Asp Ile Ile Arg Ile Ala
TAT ACC AAT TTT AGT AAT CCT TTT TCA TTT AGG GCT AAT CCA GAT ATA ATT AGA ATA GCT

                585                 590                 595                 600
Glu Glu Leu Pro Ile Arg Gly Gly Glu Leu Tyr Ile Asp Lys Ile Glu Leu Ile Leu Ala
GAA GAA CTT CCT ATT CGT GGT GGT GAG CTT TAT ATA GAT AAA ATT GAA CTT ATT CTA GCA
```

FIG.4-2

| | | | | 605 | | | | | 610 | | | | | 615 | | | | | 620 |
|---|---|---|---|---|---|---|---|---|---|---|---|---|---|---|---|---|---|---|---|
| Asp | Ala | Thr | Phe | Glu | Glu | Glu | Tyr | Asp | Leu | Glu | Arg | Ala | Gln | Lys | Ala | Val | Asn | Ala | Leu |
| GAT | GCA | ACA | TTT | GAA | GAA | GAA | TAT | GAT | TTG | GAA | AGA | GCA | CAG | AAG | GCG | GTG | AAT | GCC | CTG |

| | | | | 625 | | | | | 630 | | | | | 635 | | | | | 640 |
|---|---|---|---|---|---|---|---|---|---|---|---|---|---|---|---|---|---|---|---|
| Phe | Thr | Ser | Thr | Asn | Gln | Leu | Gly | Leu | Lys | Thr | Asp | Val | Thr | Asp | Tyr | His | Ile | Asp | Gln |
| TTT | ACT | TCT | ACA | AAT | CAA | CTA | GGG | CTA | AAA | ACA | GAT | GTG | ACG | GAT | TAT | CAT | ATT | GAT | CAA |

| | | | | 645 | | | | | 650 | | | | | 655 | | | | | 660 |
|---|---|---|---|---|---|---|---|---|---|---|---|---|---|---|---|---|---|---|---|
| Val | Ser | Asn | Leu | Val | Glu | Cys | Leu | Ser | Asp | Glu | Phe | Cys | Leu | Asp | Glu | Lys | Arg | Glu | Leu |
| GTT | TCC | AAT | TTA | GTT | GAG | TGT | TTA | TCG | GAT | GAA | TTT | TGT | CTG | GAT | GAA | AAG | AGA | GAA | TTA |

| | | | | 665 | | | | | 670 | | | | | 675 | | | | | 680 |
|---|---|---|---|---|---|---|---|---|---|---|---|---|---|---|---|---|---|---|---|
| Ser | Glu | Lys | Val | Lys | His | Ala | Lys | Arg | Leu | Ser | Asp | Glu | Arg | Asn | Leu | Leu | Gln | Asp | Pro |
| TCC | GAG | AAA | GTC | AAA | CAT | GCG | AAG | CGA | CTC | AGT | GAT | GAA | CGG | AAT | TTA | CTT | CAA | GAT | CCA |

| | | | | 685 | | | | | 690 | | | | | 695 | | | | | 700 |
|---|---|---|---|---|---|---|---|---|---|---|---|---|---|---|---|---|---|---|---|
| Asn | Phe | Arg | Gly | Ile | Asn | Arg | Gln | Pro | Asp | Arg | Gly | Trp | Arg | Gly | Ser | Thr | Asp | Ile | Thr |
| AAC | TTC | AGA | GGG | ATC | AAT | AGG | CAA | CCA | GAC | CGT | GGC | TGG | AGA | GGA | AGC | ACG | GAT | ATT | ACT |

| | | | | 705 | | | | | 710 | | | | | 715 | | | | | 720 |
|---|---|---|---|---|---|---|---|---|---|---|---|---|---|---|---|---|---|---|---|
| Ile | Gln | Gly | Gly | Asp | Asp | Val | Phe | Lys | Glu | Asn | Tyr | Val | Thr | Leu | Pro | Gly | Thr | Phe | Asp |
| ATC | CAA | GGT | GGA | GAT | GAC | GTA | TTC | AAA | GAG | AAT | TAC | GTC | ACA | TTA | CCG | GGT | ACC | TTT | GAT |

| | | | | 725 | | | | | 730 | | | | | 735 | | | | | 740 |
|---|---|---|---|---|---|---|---|---|---|---|---|---|---|---|---|---|---|---|---|
| Glu | Cys | Tyr | Pro | Thr | Tyr | Leu | Tyr | Gln | Lys | Ile | Asp | Glu | Ser | Lys | Leu | Lys | Ala | Tyr | Thr |
| GAG | TGC | TAT | CCA | ACG | TAT | TTA | TAT | CAA | AAA | ATA | GAT | GAG | TCG | AAG | TTA | AAA | GCT | TAT | ACC |

| | | | | 745 | | | | | 750 | | | | | 755 | | | | | 760 |
|---|---|---|---|---|---|---|---|---|---|---|---|---|---|---|---|---|---|---|---|
| Arg | Tyr | Glu | Leu | Arg | Gly | Tyr | Ile | Glu | Asp | Ser | Gln | Asp | Leu | Glu | Ile | Tyr | Leu | Ile | Arg |
| CGC | TAT | GAA | TTA | AGA | GGG | TAT | ATC | GAG | GAT | AGT | CAA | GAC | TTA | GAA | ATC | TAT | TTA | ATT | CGC |

| | | | | 765 | | | | | 770 | | | | | 775 | | | | | 780 |
|---|---|---|---|---|---|---|---|---|---|---|---|---|---|---|---|---|---|---|---|
| Tyr | Asn | Ala | Lys | His | Glu | Thr | Val | Asn | Val | Pro | Gly | Thr | Gly | Ser | Leu | Trp | Pro | Leu | Ser |
| TAC | AAT | GCA | AAA | CAC | GAG | ACA | GTA | AAC | GTG | CCA | GGT | ACG | GGT | TCC | TTA | TGG | CCG | CTT | TCA |

| | | | | 785 | | | | | 790 | | | | | 795 | | | | | 800 |
|---|---|---|---|---|---|---|---|---|---|---|---|---|---|---|---|---|---|---|---|
| Ala | Gln | Ser | Pro | Ile | Gly | Lys | Cys | Gly | Glu | Pro | Asn | Arg | Cys | Ala | Pro | His | Leu | Glu | Trp |
| GCC | CAA | AGT | CCA | ATC | GGA | AAG | TGT | GGA | GAA | CCG | AAT | CGA | TGC | GCG | CCA | CAC | CTT | GAA | TGG |

| | | | | 805 | | | | | 810 | | | | | 815 | | | | | 820 |
|---|---|---|---|---|---|---|---|---|---|---|---|---|---|---|---|---|---|---|---|
| Asn | Pro | Asn | Leu | Asp | Cys | Ser | Cys | Arg | Asp | Gly | Glu | Lys | Cys | Ala | His | His | Ser | His | His |
| AAT | CCT | AAT | CTA | GAT | TGC | TCC | TGC | AGA | GAC | GGG | GAA | AAA | TGT | GCC | CAT | CAT | TCC | CAT | CAT |

| | | | | 825 | | | | | 830 | | | | | 835 | | | | | 840 |
|---|---|---|---|---|---|---|---|---|---|---|---|---|---|---|---|---|---|---|---|
| Phe | Ser | Leu | Asp | Ile | Asp | Val | Gly | Cys | Thr | Asp | Leu | Asn | Glu | Asp | Leu | Gly | Val | Trp | Val |
| TTC | TCC | TTG | GAC | ATT | GAT | GTT | GGA | TGT | ACA | GAC | TTA | AAT | GAG | GAC | TTA | GGT | GTA | TGG | GTG |

| | | | | 845 | | | | | 850 | | | | | 855 | | | | | 860 |
|---|---|---|---|---|---|---|---|---|---|---|---|---|---|---|---|---|---|---|---|
| Ile | Phe | Lys | Ile | Lys | Thr | Gln | Asp | Gly | Tyr | Ala | Arg | Leu | Gly | Asn | Leu | Glu | Phe | Leu | Glu |
| ATA | TTC | AAG | ATT | AAG | ACA | CAA | GAT | GGC | TAT | GCA | AGA | CTA | GGA | AAT | CTA | GAG | TTT | CTC | GAA |

| | | | | 865 | | | | | 870 | | | | | 875 | | | | | 880 |
|---|---|---|---|---|---|---|---|---|---|---|---|---|---|---|---|---|---|---|---|
| Glu | Lys | Pro | Leu | Leu | Gly | Glu | Ala | Leu | Ala | Arg | Val | Lys | Arg | Ala | Glu | Lys | Lys | Trp | Arg |
| GAG | AAA | CCA | CTA | TTA | GGG | GAA | GCA | CTA | GCT | CGT | GTG | AAA | AGA | GCG | GAG | AAA | AAA | TGG | AGA |

FIG.4-3

```
                885                 890                 895                 900
Asp Lys Cys Glu Lys Leu Glu Trp Glu Thr Asn Ile Val Tyr Lys Glu Ala Lys Glu Ser
GAC AAA TGC GAA AAA TTG GAA TGG GAA ACA AAT ATT GTT TAT AAA GAG GCA AAA GAA TCT

                905                 910                 915                 920
Val Asp Ala Leu Phe Val Asn Ser Gln Tyr Asp Arg Leu Gln Ala Asp Thr Asn Ile Ala
GTA GAT GCT TTA TTT GTA AAC TCT CAA TAT GAT AGA TTA CAA GCG GAT ACG AAT ATC GCG

                925                 930                 935                 940
Met Ile His Ala Ala Asp Lys Arg Val His Ser Ile Arg Glu Ala Tyr Leu Pro Glu Leu
ATG ATT CAT GCG GCA GAT AAA CGC GTT CAT AGC ATT CGA GAA GCG TAT CTG CCA GAG CTG

                945                 950                 955                 960
Ser Val Ile Pro Gly Val Asn Ala Ala Ile Phe Glu Glu Leu Glu Gly Arg Ile Phe Thr
TCT GTG ATT CCG GGT GTC AAT GCG GCT ATT TTT GAA GAA TTA GAA GGG CGT ATT TTC ACT

                965                 970                 975                 980
Ala Phe Ser Leu Tyr Asp Ala Arg Asn Val Ile Lys Asn Gly Asp Phe Asn Asn Gly Leu
GCA TTC TCC CTA TAT GAT GCG AGA AAT GTC ATT AAA AAT GGC GAT TTC AAT AAT GGC TTA

                985                 990                 995                1000
Ser Cys Trp Asn Val Lys Gly His Val Asp Val Glu Glu Gln Asn Asn His Arg Ser Val
TCA TGC TGG AAC GTG AAA GGG CAT GTA GAT GTA GAA GAA CAG AAC AAC CAT CGT TCG GTC

               1005                1010                1015                1020
Leu Val Val Pro Glu Trp Glu Ala Glu Val Ser Gln Glu Val Arg Val Cys Pro Gly Arg
CTT GTT GTT CCA GAA TGG GAA GCA GAA GTG TCA CAA GAA GTT CGT GTT TGT CCG GGT CGT

               1025                1030                1035                1040
Gly Tyr Ile Leu Arg Val Thr Ala Tyr Lys Glu Gly Tyr Gly Glu Gly Cys Val Thr Ile
GGC TAT ATC CTT CGT GTT ACA GCG TAC AAA GAG GGA TAT GGA GAG GGC TGT GTA ACG ATT

               1045                1050                1055                1060
His Glu Ile Glu Asp Asn Thr Asp Glu Leu Lys Phe Ser Asn Cys Val Glu Glu Glu Val
CAT GAG ATC GAA GAC AAT ACA GAC GAA CTG AAA TTC AGC AAC TGT GTA GAA GAG GAA GTA

               1065                1070                1075                1080
Tyr Pro Asn Asn Thr Val Thr Cys Asn Asn Tyr Thr Ala Thr Gln Glu Glu His Glu Gly
TAT CCA AAC AAC ACG GTA ACG TGT AAT AAT TAT ACT GCG ACT CAA GAA GAA CAT GAG GGT

               1085                1090                1095                1100
Thr Tyr Thr Ser Arg Asn Arg Gly Tyr Asp Glu Ala Tyr Glu Ser Asn Ser Ser Val His
ACG TAC ACT TCC CGT AAT CGA GGA TAT GAC GAA GCC TAT GAA AGC AAT TCT TCT GTA CAT

               1105                1110                1115                1120
Ala Ser Val Tyr Glu Glu Lys Ser Tyr Thr Asp Arg Arg Arg Glu Asn Pro Cys Glu Ser
GCG TCA GTC TAT GAA GAA AAA TCG TAT ACA GAT AGA CGA AGA GAG AAT CCT TGT GAA TCT

               1125                1130                1135                1140
Asn Arg Gly Tyr Gly Asp Tyr Thr Pro Leu Pro Ala Gly Tyr Val Thr Lys Glu Leu Glu
AAC AGA GGA TAT GGG GAT TAC ACA CCA CTA CCA GCT GGC TAT GTG ACA AAA GAA TTA GAG

               1145                1150                1155                1160
Tyr Phe Pro Glu Thr Asp Lys Val Trp Ile Glu Ile Gly Glu Thr Glu Gly Thr Phe Ile
TAC TTC CCA GAA ACC GAT AAG GTA TGG ATT GAG ATC GGA GAA ACG GAA GGA ACA TTC ATC

               1165                1170
Val Asp Ser Val Glu Leu Leu Leu Met Glu Glu ***
GTG GAC AGC GTG GAA TTA CTT CTT ATG GAG GAA TAA TA
```

FIG.4-4

```
     1046    1050      1055      1060      1065      1070      1075      1080      1085      1090      1095      1100
HD1  E V S Q E V R V C P G R G Y I L R V T A Y K E G Y G E G C V T I H E I E N N T D E L K F S N C V E E E I Y P N
HD73 - - - - - - - - - - - - - - - - - - - - - - - - - - - - - - - - - - - - - - - - - - - - - - - - - - - - - - -
BTB  - - - - - - - - - - - - - - - - - - - - - - - - - - - - - - - - - - - - - - - - - - - - - - - - - - - V - - -
81F  - - - - - - - - - - - - - - - - - - - - - - - - - - - - - - - - - - - - D - - - - - - - - - - - - - - V - - -
BTE  - - - - - - - - - - - - - - - - - - - - - - - - - - - - - - - - - - - - D - - - - - - - - - - - - - - V - - -
HD2  - - - - A - - - - - - C - - - - - - - - - - - - - - - - - - - - - - - - - - - - - - - - K - R E - - - V - - T

     1101    1105      1110      1115      1120      1125      1130      1135      1140      1145      1150      1155
HD1  N T V T C N D Y T V N Q E E Y G G A Y T S R N R G Y N E A = = = = P S V P A D Y A S V Y E E K S Y T D G R R E
HD73 - - - - - - - - - - - - - - - - - - - - - - - - - - - - - = = = = - - - - - - - - - - - - - - - - - - - - - -
BTB  - - - - - - - - - A T - - - - E - T - - - - - - - - D G - Y E S N S - - - - - - - - A - - - - A - - - - - - -
81F  - - - - - - N - - A T - - - H E - T - - - - - - - - D - - Y = = = E - N S S V H - - - - - - - - - - - R - - -
BTE  - - - - - - N - - G T - - - - E - T - - - - - Q - - D - - Y G N N R - - - - - - - - - - - - - - - - - - - - -
HD2  D - G - - - - - - A H - G T A - *D - C N - - - A - - E D - Y E V D T T A S V N - K P T - - - E T - - - V - - -
                                      * C A

     1156    1160      1165      1170      1175      1180      1185      1190      1195
HD1  N P C E F N R G Y R D Y T P L P V G Y V T K E L E Y F P E T D K V W I E I G E T E G T F I V D S V E L L L M E
HD73 - - - - - - - - - - - - - - - - - - - - - - - - - - - - - - - - - - - - - - - - - - - - - - - - - - - - - - -
BTB  - - - - S - - - - G - - - - - - A - - - - - - - - - - - - - - - - - - - - - - - - - - - - - - - - - - - - - -
81F  - - - - S - - - - G - - - - - - A - - - - - - - - - - - - - - - - - - - - - - - - - - - - - - - - - - - - - -
BTE  - - - - S - - - - G - - - - - - A - - - - - D - - - - - - - - - - - - - - - - - - - - - - - - - - - - - - - -
HD2  - H - - Y D - - - V N Y P - V - A - - - - - - - - - - - - - - T - - - - - - - - - - K - - - - - - - - - - - -
```

FIG.5-6

HD1 is the cryA1 toxin gene from Bacillus thuringiensis subsp. kurstaki HD1 (Brizzard and Whiteley, Nucleic acids Research 16(1988)2723).

HD73 is the cryA3 gene from HD73.

BTB is the cryA2 gene from BT strain Berliner.

81F is a delta endotoxin gene from Mycogen's BT strain PS81F.

BTE is a delta endotoxin gene from BT subspecies entomocidus (Honee, Salm and Visser, Nucleic Acids Research 16(1988)6240).

HD2 is a delta endotoxin gene from BT strain HD2 (Brizzard and Whiteley, Nucleic Acids Research 16(1988)2723).

- - - - denote identical amino acid homologies.

= = = = denote gaps required to align sequences with HD1.

* denote inserts required to align the sequences BTE and HD2 with HD1.

FIG.5-7

NOVEL BACILLUS THURINGIENSIS ISOLATE DENOTED B. T. PS81F, ACTIVE AGAINST LEPIDOPTERAN PESTS, AND A GENE ENCODING A LEPIDOPTERAN-ACTIVE TOXIN

BACKGROUND OF THE INVENTION

The most widely used microbial pesticides are derived from the bacterium *Bacillus thuringiensis.* This bacterial agent is used to control a wide range of leaf-eating caterpillars, and mosquitoes. *Bacillus thuringiensis* produces a proteinaceous paraspore or crystal which is toxic upon ingestion by a susceptible insect host. For example, *B. thuringiensis* var. *kurstaki* HD-1 produces a crystal called a delta toxin which is toxic to the larvae of a number of lepidopteran insects. The cloning and expression of this *B.t.* crystal protein gene in *Escherichia coli* has been described in the published literature (Schnepf, H. E. and Whitely, H. R. [1981] *Proc. Natl. Acad. Sci.* USA 78:2893-2897). U.S. Pat. No. 4,448,885 and U.S. Pat. No. 4,467,036 both disclose the expression of *B.t.* crystal protein in *E. coli.*

BRIEF SUMMARY OF THE INVENTION

The subject invention concerns a novel *Bacillus thuringiensis* isolate designated *B.t.* PS81F which has activity against all lepidopteran pests tested.

Also disclosed and claimed is a novel toxin gene toxic to lepidopteran insects. This toxin gene can be transferred to suitable hosts via a plasmid vector.

Specifically, the invention comprises a novel *B.t.* isolate denoted *B.t.* PS81F, mutants thereof, and a novel delta endotoxin gene which encodes a 133,266 dalton protein which is active against lepidopteran pests.

DETAILED DISCLOSURE OF THE INVENTION

Figure 1:
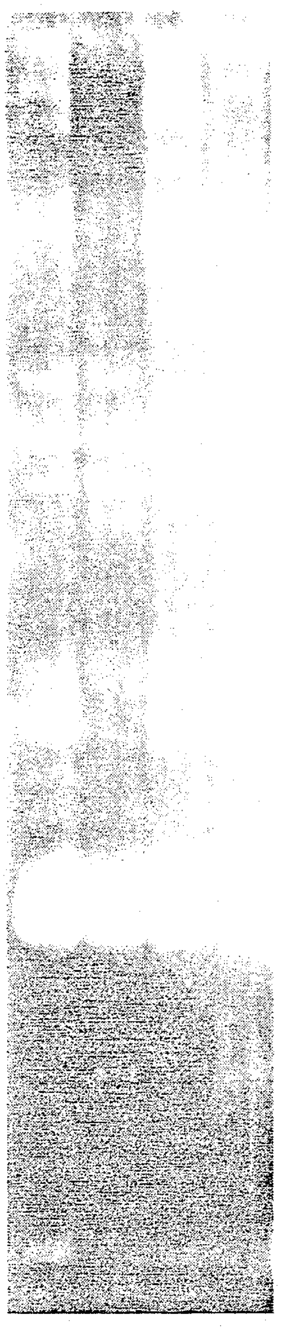
FIG. 1: Agarose gel electrophoresis of plasmid preparations from *B.t.* PS81F and *B.t.* HD-1.

The novel toxin gene of the subject invention was obtained from a novel lepidopteran-active *B. thuringiensis* (*B.t.*) isolate designated PS81F.

CHARACTERISTICS OF *B.t.* PS81F

Colony morphology—Large colony, dull surface, typical *B.t.*

Vegetative cell morphology—typical *B.t.*

Flagellar serotype-4a4c, kenya.

Intracellular inclusions—sporulating cells produce a bipyramidal crystal.

Plasmid preparations—agarose gel electrophoresis of plasmid preparations distinguishes *B.t.* PS81F from *B.t.* HD-1 and other *B.t.* isolates.

Alkali-soluble proteins—*B.t.* PS81F has a 130,000 dalton protein and a 60,000 dalton protein.

Activity—*B.t.* PS81F kills all Lepidoptera tested.

| Bioassay results: | LC50 |
|---|---|
| Beet armyworm, *Spodoptera exigua* | 10.4 ug/ml |
| Western spruce budworm, *Choristoneura occidentalis* | 1.4 ug/ml |

Bioassay procedures:

*Spodoptera exigua*—dilutions are prepared of a spore and crystal pellet, mixed with USDA Insect Diet (Technical Bulletin 1528, U.S. Department of Agriculture) and poured into small plastic trays. Neonate *Spodoptera exigua* larvae are placed on the diet mixture and held at 25° C. Mortality is recorded after six days.

*Choristoneura occidentalis*—dilutions and diet are prepared in the same manner as for the *Spodoptera exigua* bioassay. Fourth instar larvae are used, and mortality is recorded after eight days.

*B. thuringiensis* PS81F, NRRL B-18424, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against *Lepidoptera,* e.g., caterpillars. *B.t.* PS81F, and mutants thereof, can be used to control lepidopteran pests.

A subculture of *B.t.* PS81F and the *E. coli* host harboring the toxin gene of the invention, *E. coli* DH5(α), containing the plasmid pMYC386, was deposited in the permanent collection of the Northern Research Laboratory, U.S. Department of Agriculture, Peoria, Illinois, USA on October 7, 1988. The accession numbers are as follows:

*B.t.* PS81F NRRL B-18424

*E. coli* (DH5α) (pMYC386)—NRRL B-18423

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Crvptococcus, Sporobolomyces, Rhodotorula, and Aureobasidium. Of particular interest are such phytosphere bacterial species as *Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.*Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5′ to 3′ direction of the coding or sense sequence, the construct will involve the transcriptional regulatory region, if any, and the promoter, where the regulatory region may be either 5′ or 3′ of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSFIOIO, pR01614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1%-95% by weight of the pesticide while the liquid formulations will generally be from about 1%-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81F can be made by procedures well known in the art. For example, an asporogenous mutant can be obtained through ethylmethane sulfonate (EMS) mutagenesis of PS81F. The mutants can be made using ultraviolet light and nitrosoguanidine by procedures well known in the art.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t.* PS81F, NRRL B-18424

A subculture of *B.t.* PS81F, NRRL B-18424, or mutants thereof, can be used to inoculate the following medium, a peptone, glucose, salts medium:

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |

-continued

| | |
|---|---|
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Gene and Transformation into *Escherichia coli*

Total cellular DNA was prepared by growing the cells of *B. thuringiensis* HD-1 and the novel *B.t.* PS81F to a low optical density ($OD_{600}=1.0$) and recovering the cells by centrifugation. The cells were protoplasted in TES buffer (30 mM Tris-Cl, 10 mM EDTA, 50 mM NaCl, pH 8.0) containing 20% sucrose and 50 mg/ml lysozyme. The protoplasts were lysed by addition of SDS to a final concentration of 4%. The cellular material was precipitated overnight at 4° C. in 100 mM final concentration neutral potassium chloride. The supernate was extracted twice with phenol/chloroform (1:1). The DNA was precipitated in ethanol and purified by isopycnic banding on a cesium chloride gradient.

Total cellular DNA from each (PS81F and HD-1) was digested with EcoRI and separated by electrophoresis on a 0.8% Agarose-TAE-buffered gel. A Southern blot of the gel was probed with the NsiI to NsiI fragment of the toxin gene contained in plasmid pM3,130-7 of NRRL B-18332 and the NsiI to KpnI fragment of the "4.5 Kb class" toxin gene (Kronstad and Whitely [1986] Gene USA 43:29-40). These two fragments were combined and used as the probe. Results show that hybridizing fragments of PS81F are distinct from those of HD-1. Specifically, a 3.5 Kb hybridizing band in PS81F was detected instead of the 300 bp larger 3.8 Kb hybridizing band seen in HD-1.

Two hundred micrograms of PS81F total cellular DNA was digested with EcoRI and separated by electrophoresis on a preparative 0.8% Agarose-TAE gel. The 3.0 Kb to 4.0 Kb region of the gel was cut out and the DNA from it was electroeluted and concentrated using an ELUTIP™-d (Schleicher and Schuell, Keene, NH) ion exchange column. The isolated EcoRI fragments were ligated to LAMBDA ZAP™ EcoRI arms (Stratagene Cloning Systems, La Jolla, CA) and packaged using GIGAPACK GOLD™ extracts. The packaged recombinant phage were plated with *E. coli* strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BLUESCRIPT™ (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by standard miniprep procedure to find the desired plasmid. The plasmid, designated pM5,31-1, contained an approximate 3.5 Kb EcoRI insert and was sequenced using Stratagene's T7 and T3 primers plus a set of existing *B.t.* endotoxin oligonucleotide primers. About 1.7 Kb of the toxin gene was sequenced and data analysis comparing PS81F to other cloned *B.t.* endotoxin genes showed that the PS81F sequence was unique. A synthetic oligonucleotide (GCTGAAGAACTTCCTATTCGTGGTGGTGAGC) was constructed to one of the regions in the PS81F sequence that was least homologous relative to other existing *B.t.* endotoxin genes.

Total cellular DNA partially digested with Sau3A and fractionated by electrophoresis into a mixture of 9-23 Kb fragments on a 0.6% agarose TAE gel was ligated into LAMBDA DASH™(Stratagene). The packaged phage were plated out with P2392 *E. coli* cells (Stratagene) at a high titer and screened using the radiolabeled synthetic oligonucleotide supra as a nucleic acid hybridization probe. Hybridizing plaques were rescreened at a lower plaque density. A purified hybridizing plaque was used to infect P2392 *E. coli* cells in liquid culture for preparation of phage for DNA isolation. DNA was isolated by standard procedures. Preparative amounts of recombinant phage DNA were digested with SalI (to release the inserted DNA from lambda arms) and separated by electrophoresis on a 0.6% Agarose-TAE gel. The large fragments (electroeluted and concentrated as described above) were ligated to an XhoI digested and phosphatased BLUESCRIPT™plasmid. The ligation was transformed into *E. coli* DH5($\alpha$) competent cells (BRL) and plated on LB agar containing ampicillin, isopropyl-($\beta$)-D-thiogalactoside (IPTG) and 5-bromo-4-chloro-3-indolyl-($\beta$)-D-galactoside (XGAL). White colonies (with insertions in the ($\beta$)-galactosidase gene of pBluescript) were subjected to standard miniprep procedures to isolate the plasmid, designated pMI,43-24. The full length toxin gene was sequenced by using oligonucleotide primers made to the "4.3 Kb class" toxin gene and by "walking" with primers made to the sequence of PS81F. Data analysis comparing the deduced PS81F amino acid sequence to the sequences of five other endotoxins shows PS81F to be unique (Table 4).

The plasmid pM1,43-24 contains about 18 Kb of PS81F DNA including the 3.518 Kb which codes for the 133,266 dalton endotoxin. The plasmid was reduced in size by cutting out approximately 13 Kb of non-coding DNA, ligating the ends, transforming DH5($\alpha$) and plating on LB agar containing ampicillin. The resulting colonies were analyzed by standard miniprep procedures to isolate plasmids that were reduced in size. The desired plasmid, pMYC386, contains the coding sequence of the PS81F toxin gene, which could be excised as an SaeI to ApaI 4.5 Kb fragment.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, MD, or New England Biolabs, Beverly, MA. The enzymes are used according to the instructions provided by the supplier.

Plasmid pMYC386 containing the *B.t.* toxin gene, can be removed from the transformed host microbe by use of standard well-known procedures. For example, *E. coli* NRRL B-18423 can be subjected to cleared lysate isopycnic density gradient procedures, and the like, to recover pMYC386.

Data from standard insect tests show that novel *B.t.* PS81F is active against diamondback moth, *Spodoptera exigua,* Western spruce budworm, and *T. ni.*

EXAMPLE 3

Insertion of Toxin Gene Into Plants

The novel gene coding for the novel insecticidal toxin, as disclosed herein, can be inserted into plant cells using the Ti plasmid from *Agrobacter tumefaciens.* Plant cells can then be caused to regenerate into plants (Zambryski, P., Joos, H., Gentello, C., Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in *E. coli,* and transformed into appropriate plant cells.

EXAMPLE 4

Cloning of Novel B. *thuringiensis* Gene Into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399-406), and pAC380, described by Smith et al. (Smith, G. E., Summers, M. D. and Fraser, M. J. [1983] Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequence encoding the novel *B.t.* toxin gene is shown in Table 1. The deduced amino acid sequence is shown in Table 2.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A =adenine
G =guanine
C =cytosine
T =thymine
X =T or C if Y is A or G
X =C if Y is C or T
Y =A, G, C or T if X is C
Y =A or G if X is T
W =C or A if Z is A or G
W - C if Z is C or T
Z =A, G, C or T if W is C
Z =A or G if W is A
QR =TC if S is A, G, C or T; alternatively QR =AG if S is T or C
J =A or G
K =T or C
L =A, T, C or G
M =A, C or T The above shows that the novel amino acid sequence of the *B.t.* toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249-255). Thus, the subject invention includes mutants of the amino acid sequence depicted herein which do not alter the protein secondary structure, or if the structure is altered, the biological activity is retained to some degree.

We claim:

1. DNA encoding a *B.t.* toxin having the amino acid, sequence shown in FIG. 3.

Figures 1, 5:
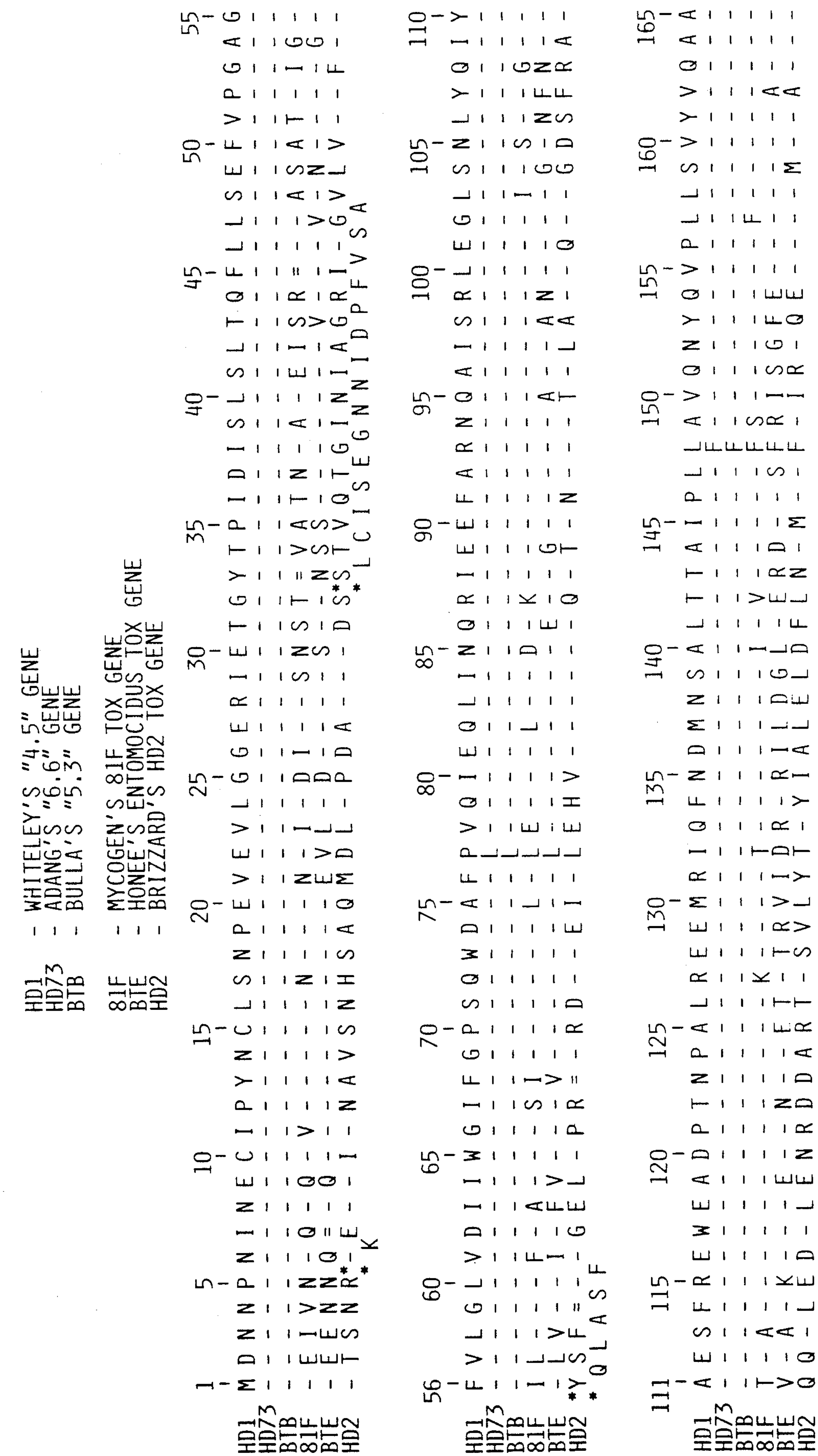
FIG. 5(1-7): A comparison of the deduced amino acid sequence of 81F and five other known *B.t.* endotoxins.
Figures 2, 5:
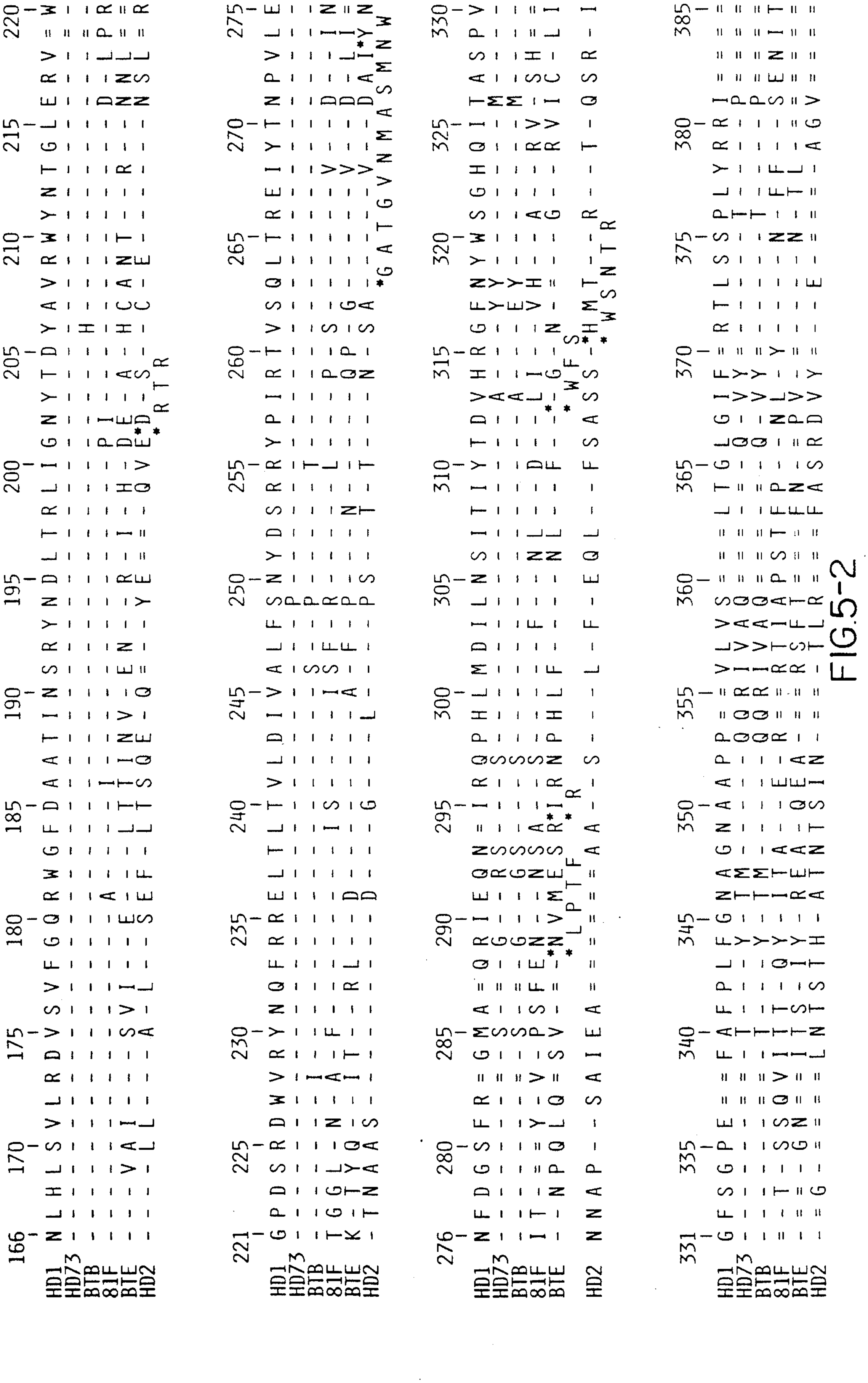
FIG. 2 (1-2): Nucleotide sequence of novel toxin encoding gene.

2. DNA, according to claim 1, having the nucleotide sequence shown in FIG. 2.

3. A recombinant DNA transfer vector comprising DNA having the nucleotide sequence which codes for the amino acid sequence shown in FIG. 3.

4. The DNA transfer vector, according to claim 3, transferred to and replicated in a prokaryotic or eukaryotic host.

5. A bacterial host transformed to express a *B.t.* toxin having the amino acid sequence shown in Table 2.

Figures 3, 5:
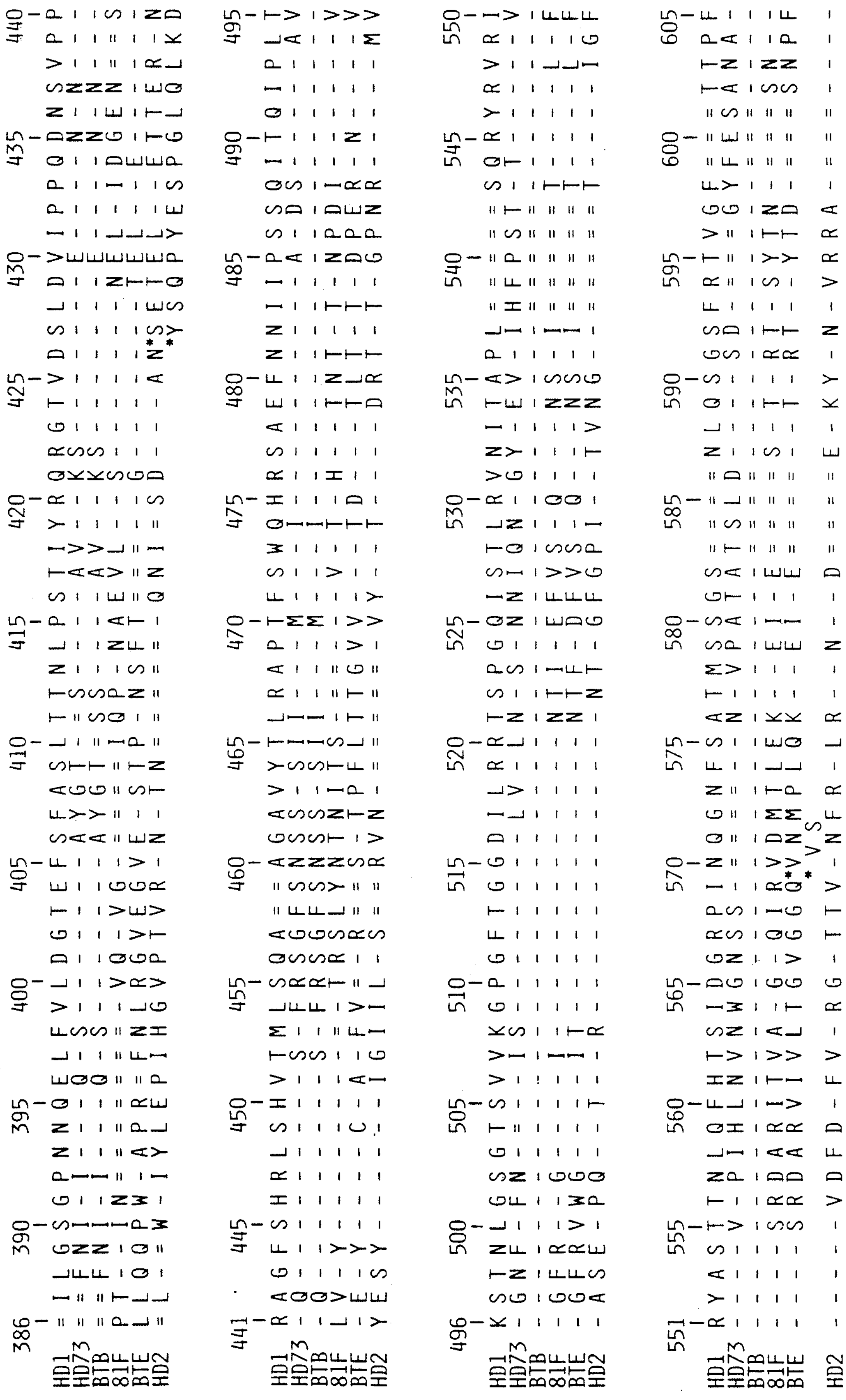
FIG. 3(1-2): Deduced amino acid sequence of novel toxin.
Figures 4, 5:
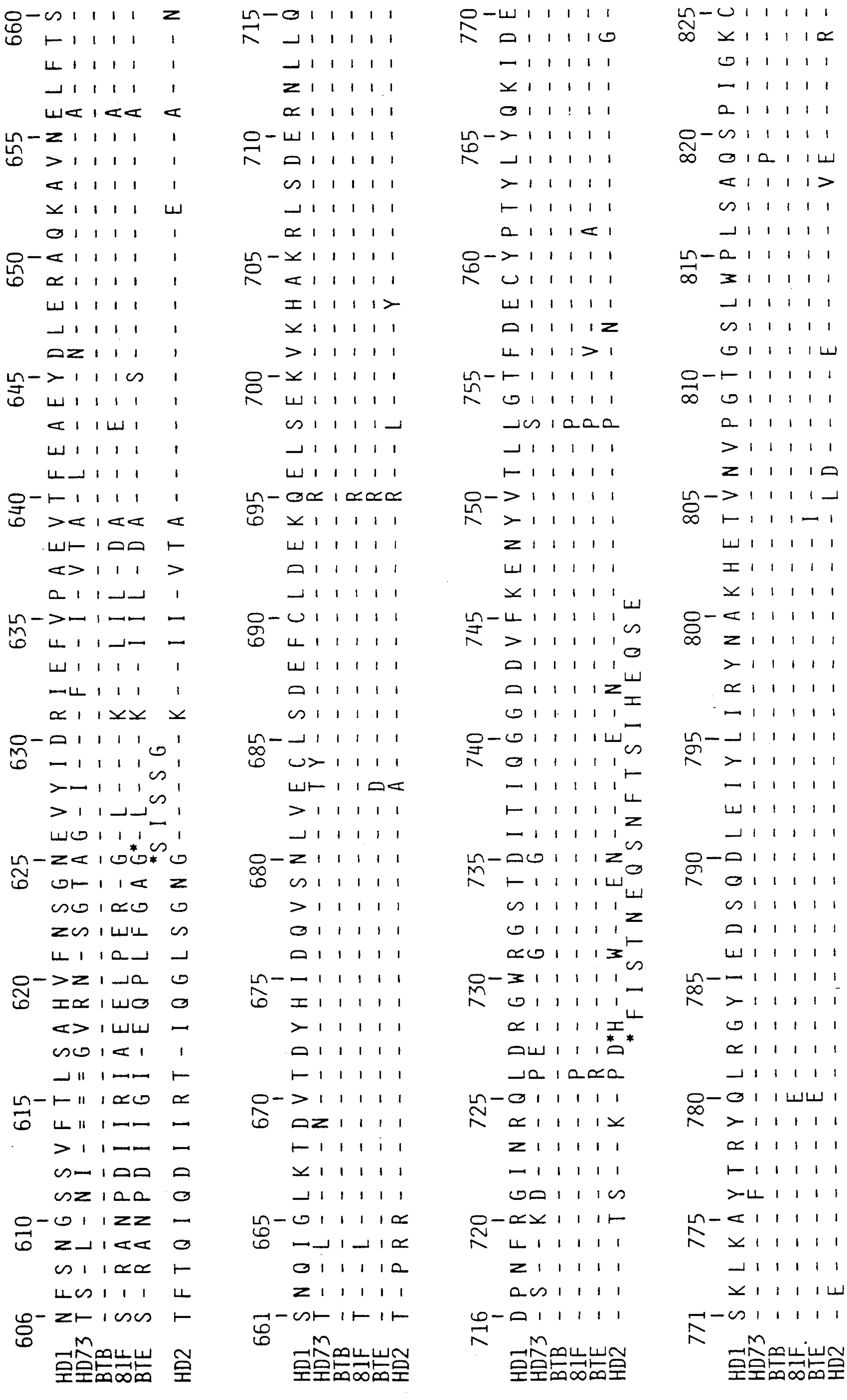
FIG. 4(1-4): Nucleotide sequence of novel toxin encoding gene and deduced amino acid sequence of novel toxin.
Figure 5:
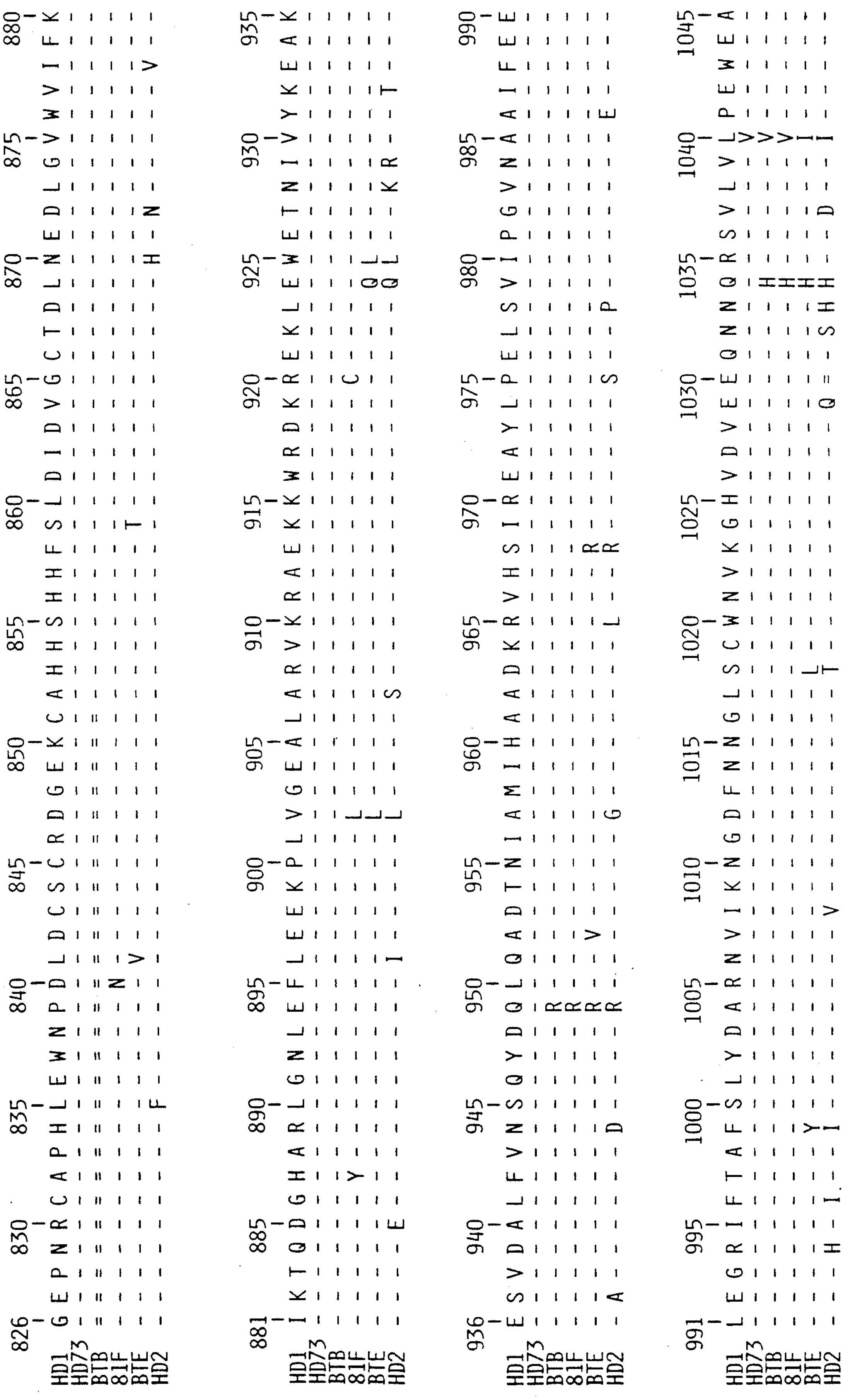

6. *Escherichia coli*, according to claim 5, transformed with a plasmid vector containing the *B.t.* toxin gene encoding the *B.t.* toxin having the amino acid sequence shown in FIG. 3.

7. *E. coli* DH5(α) (pMYC386), having the identifying characteristics of NRRL B-18423, a host according to claim 5.

8. A microorganism according to claim 5, which is a species of Pseudomonas, Azotobacter, Erwinia, Serratia, Klebsiella, Rhizobium, Rhodopseudomonas, Methylophilius, Agrobacterium, Acetobacter or Alcaligenes.

9. A microorganism according to claim 8, wherein said microorganism is pigmented and phylloplane adherent.

10. Plasmic denoted pMYC386.

* * * * *

UNITED STATES PATENT AND TRADEMARK OFFICE
CERTIFICATE OF CORRECTION

PATENT NO. : 5,045,469

DATED : Sept. 3, 1991

INVENTOR(S) : Jewel M. Payne and August J.Sick

It is certified that error appears in the above-identified patent and that said Letters Patent is hereby corrected as shown below:

Column 1, line 37, "Brief Description of the Drawing" should read --Brief Description of the Drawings--.

Column 3, line 43, "Crptococcus, Sporobolomyces" should read --Cryptococcus, Kluveromyces, Sporobolomyces--.

Column 5, line 33, "RSFIOIO" should read --RSF1010--.

Signed and Sealed this

Third Day of August, 1993

*Attest:*

MICHAEL K. KIRK

*Attesting Officer*

*Acting Commissioner of Patents and Trademarks*

UNITED STATES PATENT AND TRADEMARK OFFICE

CERTIFICATE OF CORRECTION

PATENT NO. : 5,045,469

DATED : September 3, 1991

INVENTOR(S) : Jewel Payne and August J. Sick

It is certified that error appears in the above-indentified patent and that said Letters Patent is hereby corrected as shown below:

Column 12, line 30: Delete "Table 2" and insert --Figure 3--.

Signed and Sealed this

First Day of March, 1994

Attest:

BRUCE LEHMAN

Attesting Officer

Commissioner of Patents and Trademarks